(12) United States Patent
Thompson

(10) Patent No.: US 12,416,021 B1
(45) Date of Patent: Sep. 16, 2025

(54) COMPOSITION FOR REGULATING PRODUCTION OF PROTEINS

(71) Applicant: Wyvern Pharmaceuticals Inc., Calgary (CA)

(72) Inventor: Bradley G. Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 0 days.

(21) Appl. No.: 18/913,027

(22) Filed: Oct. 11, 2024

(51) Int. Cl.
| | |
|---|---|
| *A61K 48/00* | (2006.01) |
| *A61K 38/18* | (2006.01) |
| *C07K 14/51* | (2006.01) |
| *C12N 15/11* | (2006.01) |
| *C12N 15/86* | (2006.01) |
| *C12N 15/864* | (2006.01) |

(52) U.S. Cl.
CPC .............. *C12N 15/86* (2013.01); *C07K 14/51* (2013.01); *C12N 2750/14143* (2013.01)

(58) Field of Classification Search
None
See application file for complete search history.

(56) References Cited

U.S. PATENT DOCUMENTS

| | | |
|---|---|---|
| 11,085,055 B2 | 8/2021 | Mallol et al. |
| 11,530,423 B1 | 12/2022 | Thompson |
| 11,873,505 B2 | 1/2024 | Thompson |
| 12,018,274 B2 | 6/2024 | Thompson |
| 12,134,770 B1 | 11/2024 | Thompson |
| 2020/0362344 A1 | 11/2020 | Minshull et al. |
| 2022/0356489 A1 | 11/2022 | Thompson |
| 2024/0026377 A1 | 1/2024 | Thompson |

FOREIGN PATENT DOCUMENTS

| | | | |
|---|---|---|---|
| CA | 2721333 A1 | 10/2009 | |

OTHER PUBLICATIONS

O'Brien et al. "Overview of microRNA biogenesis, mechanisms of actions, and circulation." Frontiers in endocrinology 9 (2018): 402, pp. 1-12.
Gorski et al. "RNA-based recognition and targeting: sowing the seeds of specificity." Nature Reviews Molecular Cell Biology 18.4 (2017): 215-228.
Bottoni et al. "Targeting BTK through microRNA in chronic lymphocytic leukemia." Blood, The Journal of the American Society of Hematology 128.26 (2016): 3101-3112.
Christensen et al. "Recombinant adeno-associated virus-mediated microRNA delivery into the postnatal mouse brain reveals a role for miR-134 in dendritogenesis in vivo." Frontiers in neural circuits 3 (2010): 848, pp. 1-10.
Bofill-De Ros et al. "Guidelines for the optimal design of miRNA-based shRNAs." Methods 103 (2016): 157-166.
Denzler et al. "Impact of microRNA levels, target-site complementarity, and cooperativity on competing endogenous RNA-regulated gene expression." Molecular cell 64.3 (2016): 565-579.
Van Den Berg et al. "Design of effective primary microRNA mimics with different basal stem conformations." Molecular Therapy Nucleic Acids 5 (2016), pp. 1-12.
Tritschler et al. "Concepts and limitations for learning developmental trajectories from single cell genomics." Development 146.12 (2019): dev170506, pp. 1-12.
Ahmadzadeh et al. "BRAF mutation in hairy cell leukemia." Oncology reviews 8.2 (2014): 253, pp. 1-4.
Patton et al. "Biogenesis, delivery, and function of extracellular RNA." Journal of extracellular vesicles 4.1 (2015): 27494, pp. 1-3.
Clark et al. "Detection of BRAF splicing variants in plasma-derived cell-free nucleic acids and extracellular vesicles of melanoma patients failing targeted therapy therapies." Oncotarget 11.44 (2020): 4016, pp. 4016-4027.
Wang et al. "Adeno-associated virus vector as a platform for gene therapy delivery." Nature reviews Drug discovery 18.5 (2019): 358-378.
Kondratov et al. "Direct head-to-head evaluation of recombinant adeno-associated viral vectors manufactured in human versus insect cells." Molecular Therapy 25.12 (2017): 2661-2675.
Nature (2010. Gene Expression. Scitable. Available online at Nature. com) <nature.com/scitable/topicpage/gene-expression-14121669> (2010), pp. 1-6.
Brutons Tyrosine Kinase Genbank Sequence (2023), pp. 1-9.
GenBank EGFR Sequence (2023), pp. 11-23.
GenBank EGF Sequence (2023), pp. 1-9.
NCBI search results for SEQ ID No. 5 (2024), pp. 1-15.
NCBI Nucleotide Sequence ALK Lingand, search performed Dec. 26, 2024 (2023), pp. 1-6.
NCBI Nucleotide Sequence ALK Receptor, search performed Dec. 26, 2024 (2023), pp. 1-16.
NCBI Nucleotide Sequence for PARP, search performed Dec. 26, 2024 (2024), pp. 1-9.
GenBank FLT3 Sequence (2024), pp. 1-14.

*Primary Examiner* — Maria Marvich
(74) *Attorney, Agent, or Firm* — Gowling WLG (Canada) LLP

(57) ABSTRACT

Some embodiments of the present disclosure relate to one or more compositions that upregulate the production of one or more sequences of mRNA. The sequences of mRNA may encode for translation of a target biomolecule, thereby causing an increase in the bioavailability of the target biomolecule within a subject that is administered the one or more compositions. In some embodiments of the present disclosure, the target biomolecule is a protein such as BMP11.

7 Claims, No Drawings

Specification includes a Sequence Listing.

```
                               SEQUENCE LISTING

Sequence total quantity: 3
SEQ ID NO: 1           moltype = DNA  length = 5930
FEATURE                Location/Qualifiers
source                 1..5930
                       mol_type = other DNA
                       organism = synthetic construct
SEQUENCE: 1
aatcaacctc tggattacaa aatttgtgaa agattgactg gtattcttaa ctatgttgct   60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt cccctccct   300
attgccacgg cggaactcat cgccgcctgc cttgcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttcctc ccgcggcctg ctgccggctc tgcggcctct tccgcgtctt  540
cgccttcgcc ctcagacgag tcggatctct ctttgggccg cctccccgcc taagcttatc  600
gataccgtcg agatctaact tgtttattgc agcttataat ggttacaaat aaagcaatag  660
catcacaaat ttcacaaata aagcattttt ttcactgcat tctagttgtg gtttgtccaa  720
actcatcaat gtatcttatc atgtctggat ctcgacctcg actagagcat ggctacgtag  780
ataagtagca tggcgggtta atcattaact acaaggaacc cctagtgatg gagttggcca  840
ctccctctct gcgcgctcgc tcgctcactg aggccgggca accaaaggtc gcccgacgcc  900
cgggctttgc ccgggcggcc tcagtgagcg agcgagcgcg ccagctggcg taatagcgaa  960
gaggcccgca ccgatcgccc ttcccaacag ttgcgcagcc tgaatggcga atggaattcc 1020
agacgattga gcgtcaaaat gtaggtattt ccatgagcgt ttttcctgtt gcaatggctg 1080
gcggtaatat tgttctggat attaccagca aggccgatag tttgagttct tctactcagg 1140
caagtgatgt tattactaat caaagaagta ttgcgacaac ggttaatttg cgtgatggac 1200
agactctttt actcggtggc ctcactgatt ataaaaacac ttctcaggat tctggcgtac 1260
cgttcctgtc taaaatccct ttaatcggcc tcctgtttag ctcccgctct gattctaacg 1320
aggaaagcac gttatacgtg ctcgtcaaag caaccatagt acgcgccctg tagcggcgca 1380
ttaagcgcgg cgggtgtggt ggttacgcgc agcgtgaccg ctacacttgc cagcgcccta 1440
gcgcccgctc ctttcgcttt cttcccttcc tttctcgcca cgttcgccgg ctttccccgt 1500
caagctctaa atcgggggct cccttagggg ttccgattta gtgctttacg gcacctcgac 1560
cccaaaaaac ttgattaggg tgatggttca cgtagtgggc catcgccctg atagacggtt 1620
tttcgccctt tgacgttgga gtccacgttc tttaatagtg gactcttgtt ccaaactgga 1680
acaacactca accctatctc ggtctattct tttgatttat aagggatttt gccgatttcg 1740
gcctattggt taaaaaatga gctgatttaa caaaaattta acgcgaattt taacaaaata 1800
ttaacgttta caatttaaat atttgcttat acaatcttcc tgttttgg gcttttctga 1860
ttatcaaccg gggtacatat gattgacatg ctagttttac gattaccgtt catcgattct 1920
cttgtttgct ccagactctc aggcaatgac ctgatagcct ttgtagagac ctctcaaaaa 1980
tagctaccct ctccggcatg aatttatcag ctagaacggt tgaatatcat attgatggtg 2040
atttgactgt ctccggcctt tctcacccgt ttgaatcttt acctacacat tactcaggca 2100
ttgcatttaa aatatatgag ggttctaaaa atttttatcc ttgcgttgaa ataaaggctt 2160
ctcccgcaaa agtattacag ggtcataatg ttttggtac aaccgattta gctttatgct 2220
ctgaggcttt attgcttaat tttgctaatt cttttgccttg cctgtatgat ttattggata 2280
ttggaattcc tgatgcggta ttttctcctt acgcatctgt gcggtatttc acaccgcata 2340
tggtgcactc tcagtacaat ctgctctgat gccgcatagt taagccagcc ccgacacccg 2400
ccaacacccg ctgacgcgcc ctgacgggct tgtctgctcc cggcatccgc ttacagacaa 2460
gctgtgaccg tctccgggag ctgcatgtgt cagaggtttt caccgtcatc accgaaacgc 2520
gcgagacgaa agggcctcgt gatacgccta tttttaatagg ttaatgtcat gataataatg 2580
gtttcttaga cgtcaggtgg cacttttcgg ggaaatgtgc gcggaacccc tatttgttta 2640
tttttctaaa tacattcaaa tatgtatccg ctcatgagac aataaccctg ataaatgctt 2700
caataatatt gaaaaaggaa gagtatgagt attcaacatt tccgtgtcgc ccttattccc 2760
ttttttgcgg catttttgcct tcctgttttt gctcacccag aaacgctggt gaaagtaaaa 2820
gatgctgaag atcagttggg tgcacgagtg gttacatcg aactggatct caacagcggt 2880
aagatccttg agagttttcg ccccgaagaa cgttttccaa tgatgagcac ttttaaagtt 2940
ctgctatgtg gcgcggtatt atcccgtatt gacgccggc aagagcaact cggtcgccgc 3000
atacactatt ctcagaatga cttggttgag tactcaccag tcacagaaaa gcatcttacg 3060
gatggcatga cagtaagaga attatgcagt gctgccataa ccatgagtga taacactgcg 3120
gccaacttac ttctgacaac gatcggagga ccgaaggagc taaccgcttt tttgcacaac 3180
atgggggatc atgtaactcg ccttgatcgt tgggaaccgg agctgaatga agccatacca 3240
aacgacgagc gtgacaccac gatgcctgta gcaatggcaa caacgttgcg caaactatta 3300
actggcgaac tacttactct agcttcccgg caacaattaa tagactggat ggaggcggat 3360
aaagttgcag gaccacttct gcgctcggcc cttccggctg gctggtttat tgctgataaa 3420
tctggagccg gtgagcgtgg gtctcgcggt atcattgcag cactggggcc agatggtaag 3480
ccctcccgta tcgtagttat ctacacgacg gggagtcagg caactatgga tgaacgaaat 3540
agacagatcg ctgagatagg tgcctcactg attaagcatt ggtaactgtc agaccaagtt 3600
tactcatata tactttagat tgatttaaaa cttcatttt aatttaaaag gatctaggtg 3660
aagatccttt ttgataatct catgaccaaa atcccttaac gtgagttttc gttccactga 3720
gcgtcagacc ccgtagaaaa gatcaaagga tcttcttgag atcctttttt tctgcgcgta 3780
atctgctgct tgcaaacaaa aaaaccaccg ctaccagcgg tggtttgttt gccggatcaa 3840
gagctaccaa ctctttttcc gaaggtaact ggcttcagca gagcgcagat accaaatact 3900
gtccttctag tgtagccgta gttaggccac cacttcaaga actctgtagc accgcctaca 3960
```

```
tacctcgctc tgctaatcct gttaccagtg gctgctgcca gtggcgataa gtcgtgtctt    4020
accgggttgg actcaagacg atagttaccg gataaggcgc agcggtcggg ctgaacgggg    4080
ggttcgtgca cacagcccag cttggagcga acgacctaca ccgaactgag atacctacag    4140
cgtgagctat gagaaagcgc cacgcttccc gaagggagaa aggcggacag gtatccggta    4200
agcggcaggg tcggaacagg agagcgcacg agggagcttc caggggggaaa cgcctggtat    4260
ctttatagtc ctgtcgggtt tcgccacctc tgacttgagc gtcgattttt gtgatgctcg    4320
tcaggggggc ggagcctatg gaaaaacgcc agcaacgcgg cctttttacg gttcctggcc    4380
ttttgctggc cttttgctca catgttcttt cctgcgttat cccctgattc tgtggataac    4440
cgtattaccg cctttgagtg agctgatacc gctcgccgca gccgaacgac cgagcgcagc    4500
gagtcagtga gcgaggaagc ggaagagcgc ccaatacgca aaccgcctct ccccgcgcgt    4560
tggccgattc attaatgcag cagctgcgcg ctcgctcgct cactgaggcc gcccgggcaa    4620
agcccggggc tcgggcgacc tttggtcgcc cggcctcagt gagcgagcga gcgcgcagag    4680
agggagtggc caactccatc actaggggtt ccttgtagtt aatgattaac cgccatgtt    4740
acttatctac gtagccatgc tctaggacat tgattattga ctagtggagt tccgcgttac    4800
ataacttacg gtaaatggcc cgcctggctg accgcccaac gaccccgcc cattgacgtc    4860
aataatgacg tatgttccca tagtaacgcc aatagggact ttccattgac gtcaatgggt    4920
ggagtattta cggtaaactg cccacttggc agtacatcaa gtgtatcata tgccaagtac    4980
gccccctatt gacgtcaatg acggtaaatg gcccgcctgg cattatgccc agtacatgac    5040
cttatgggac tttcctactt ggcagtacat ctacgtatta gtcatcgcta ttaccatggt    5100
cgaggtgagc cccacgttct gcttcactct ccccatctcc ccccctccc cacccccaat    5160
tttgtattta tttatttttt aattattttg tgcagcgatg ggggcggggg gggggggggg    5220
cgcgcgccag gcggggcggg gcggggcgag gggcggggcg gagggaggcg gagaggtgcg    5280
gcggcagcca atcagagcgg cgcgctccga aagtttcctt ttatggcgag gcggcggcgg    5340
cggcggccct ataaaaagcg aagcgcgcgg cgggcgggag tcgctgcgcg ctgccttcgc    5400
cccgtgcccc gctccgccgc cgcctcgcgc cgcccgcccc ggctctgact gaccgcgtta    5460
ctaaaacagg taagtccggc ctccgcgccg ggttttggcg cctcccgcgg gcgcccccct    5520
cctcacggcg agcgctgcca cgtcagacga agggcgcagc gagcgtcctg atccttccgc    5580
ccggacgctc aggacagcgg cccgctgctc ataagactcg gccttagaac cccagtatca    5640
gcagaaggac attttaggac gggacttggg tgactctagg cactggtttt tctttccaga    5700
gagcggaaca gcgaggaaa agtagtccct tctcggcgat tctgcggagg gatctccgtg    5760
gggcggtgaa cgccgatgat gcctctacta accatgttca tgttttcttt ttttttctac    5820
aggtcctggg tgacgaacag ggtaccgcca ccatgcgcac gggttcaaga acttccctac    5880
ttcttgcatt tggcctgctt tgtttgccgt ggttacagga gggctcggca               5930

SEQ ID NO: 2           moltype = DNA  length = 1230
FEATURE                Location/Qualifiers
source                 1..1230
                       mol_type = other DNA
                       organism = synthetic construct
SEQUENCE: 2
atggtgctgg cggcgccgct gctgctgggc tttctgctgc tggcgctgga actgcgcccg     60
cgcggcgaag cggcggaagg cccggcgcg gcggcggcgg cggcggcggc ggcggcggcg    120
gcgggcgtgg gcggcgaacg cagcagccgc ccggcgcgca gcgtggcgcc ggaaccggat    180
ggctgcccgg tgtgcgtgtg cgcgcagcat agccgcgaac tgcgcctgga agcattaaaa    240
agccagattc tgagcaaact gcgcctgaaa gaagcgccga acattagccg cgaagtggtg    300
aaacagctgc tgccgaaagc gccgccgctg cagcagattc tggatctgca tgattttcag    360
ggcgatgcgc tgcagccgga agattttctg gaagaagatg aatatcatgc gaccaccgaa    420
accgtgatta gcatggcgca ggaaaccgat ccgcgcggtg cagaccgatg cagcccgctg    480
tgctgccatt tcattttttag cccgaaagtg atgtttacca aagtgctgaa agcgcagctg    540
tgggtgtatc tgcgcccggt gccgcgcccg gcgaccgtgt atctgcagat tctgcgcctg    600
aaaccgctga ccggcgaagg caccgcgggc ggcggcggcg gcggccgcg ccatattgc     660
attcgcagcc tgaaaattga actgcatagc cgcagcggcc attggcagag cattgatttt    720
aaacaggtgc tgcatagctg gtttcgccag ccgcagagca ctggggcat tgaaattaac    780
gcgtttgatc gagcggcac cgatctggcg gtgaccagcc tgggcccggg cgcggaaggc    840
ctgcatccgt ttatggaact gcgccgtgctg gaaaaaccaa agcagccg ccgcaacctg    900
ggcctggatt gcgatgaaca tagcagccaa agccgctgct gccgctatcc gctgaccgtg    960
gatttttgaag cgtttggctg ggattggatt attgcgccga aacgctataa agcgaactat   1020
tgcagcggcc agtgcgaata tatgtttatg cagaaatatc gcataccca tctggtgcag   1080
caggcgaaacc cgcgcggcag cgcgggcccg tgctgcaccc cgaccaaaat gagcccgatt   1140
aacatgctgt attttaacga taaacagcag attatttatg gcaaaattcc gggcatggtg   1200
gtggatcgct gcggctgcag ctctagagat                                    1230

SEQ ID NO: 3           moltype = DNA  length = 7160
FEATURE                Location/Qualifiers
source                 1..7160
                       mol_type = other DNA
                       organism = synthetic construct
SEQUENCE: 3
aatcaacctc tggattacaa aatttgtgaa agattgactg gtattcttaa ctatgttgct     60
cctttacgc tatgtggata cgctgcttta atgcctttgt atcatgctat tgcttcccgt    120
atggctttca tttttcctc cttgtataaa tcctggttgc tgtctcttta tgaggagttg    180
tggcccgttg tcaggcaacg tggcgtggtg tgcactgtgt ttgctgacgc aaccccact    240
ggttgggca ttgccaccac ctgtcagctc ctttccggga cttcgctttt ccccctcct    300
attgccagc cggaactcat cgccgcctgc cttgcccgct gctggacagg ggctcggctg    360
ttgggcactg acaattccgt ggtgttgtcg gggaaatcat cgtccttcc ttggctgctc    420
gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc taagcttatc    600
gataccgtcg agatctaact tgtttattgc agcttataat ggttacaaat aaagcaatag    660
```

```
catcacaaat ttcacaaata aagcattttt ttcactgcat tctagttgtg gtttgtccaa    720
actcatcaat gtatcttatc atgtctggat ctcgacctcg actagagcat ggctacgtag    780
ataagtagca tggcgggtta atcattaact acaaggaacc cctagtgatg gagttggcca    840
ctccctctct gcgcgctcgc tcgctcactg aggccgggcg accaaaggtc gcccgacgcc    900
cgggctttgc ccgggcggcc tcagtgagcg agcgagcgcg ccagctgcgt taatagcgaa    960
gaggcccgca ccgatcgccc ttcccaacag ttgcgcagcc tgaatggcga atggaattcc   1020
agacgattga gcgtcaaaat gtaggtattt ccatgagcgt ttttcctgtt gcaatggctg   1080
gcggtaatat tgttctggat attaccagca aggccgatag tttgagttct tctactcagg   1140
caagtgatgt tattactaat caaagaagta ttgcgacaac ggttaatttg cgtgatggac   1200
agactctttt actcggtggc ctcactgatt ataaaaacac ttctcaggat tctggcgtac   1260
cgttcctgtc taaaatccct ttaatcggcc tcctgtttag ctcccgctct gattctaacg   1320
aggaaagcac gttatacgtg ctcgtcaaag caaccatagt acgcgccctg tagcggcgca   1380
ttaagcgcgg cgggtgtggt ggttacgcgc agcgtgaccg ctacacttgc cagcgcccta   1440
gcgcccgctc ctttcgcttt cttcccttcc tttctcgcca cgttcgccgg ctttccccgt   1500
caagctctaa atcgggggct ccctttaggg ttccgattta gtgctttacg gcacctcgac   1560
cccaaaaaac ttgattaggg tgatggttca cgtagtgggc catcgccctg atagacggtt   1620
tttcgccctt tgacgttgga gtccacgttc tttaatagtg gactcttgtt ccaaactgga   1680
acaacactca accctatctc ggtctattct tttgatttat aagggatttt gccgatttcg   1740
gcctattggt taaaaatga gctgatttaa caaaaattta acgcgaattt taacaaaata   1800
ttaacgttta caatttaaat atttgcttat acaatcttcc tgttttttggg gcttttctga   1860
ttatcaaccg gggtacatat gattgacatg ctagttttac gattaccgtt catcgattct   1920
cttgtttgct ccagactctc aggcaatgac ctgatagcct ttgtagagac tctcaaaaa    1980
tagctaccct ctccggcatg aatttatcag ctagaacggt tgaatatcat attgatggt    2040
atttgactgt ctccggcctt tctcacccgt ttgaatcttt acctacacat tactcaggca   2100
ttgcatttaa aatatatgag ggttctaaaa atttttatcc ttgcgttgaa ataaaggctt   2160
ctcccgcaaa agtattacag ggcataatg tttttggtac aaccgattta gctttatgct    2220
ctgaggcttt attgcttaat tttgctaatt ctttgccttg cctgtatgat ttattggatg   2280
ttggaattcc tgatgcggta ttttctcctt acgcatctgt gcggtatttc acaccgcata   2340
tggtgcactc tcagtacaat ctgctctgat gccgcatagt taagccagcc ccgacacccg   2400
ccaacacccg ctgacgcgcc ctgacgggct tgtctgctcc cggcatccgc ttacagacaa   2460
gctgtgaccg tctccgggag ctgcatgtgt cagaggtttt caccgtcatc accgaaacgc   2520
gcgagacgaa agggcctcgt gatacgccta ttttataggt taatgtcat gataataatg    2580
gtttcttaga cgtcaggtgg cacttttcgg ggaaatgtgc gcggaacccc tatttgttta   2640
tttttctaaa tacattcaaa tatgtatccg ctcatgagac aataaccctg ataaatgctt   2700
caataatatt gaaaaaggaa gagtatgagt attcaacatt tccgtgtcgc ccttattccc   2760
ttttttgcgg cattttgcct tcctgttttt gctcacccag aaacgctggt gaaagtaaaa   2820
gatgctgaag atcagttggg tgcacgagtg ggttacatcg aactggatct caacagcggt   2880
aagatcctg agagttttcg ccccgaagaa cgttttccaa tgatgagcac ttttaaagtt    2940
ctgctatgtg gcgcggtatt atcccgtatt gacgccggca agagcaact cggtcgccga    3000
atacactatt ctcagaatga cttggttgag tactcaccag tcacagaaaa gcatcttacg   3060
gatggcatga cagtaagaga attatgcagt gctgccataa ccatgagtga taacactgcg   3120
gccaacttac ttctgacaac gatcggagga ccgaaggagc taaccgcttt tttgcacaac   3180
atgggggatc atgtaactcg ccttgatcgt tgggaaccgg agctgaatga agccatacca   3240
aacgacgagc gtgacaccac gatgcctgta gcaatggcaa caacgttgcg caaactatta   3300
actggcgaac tacttactct agcttcccgg caacaattaa tagactggat ggaggcggat   3360
aaagttgcag gaccacttct gcgctcggcc cttccggctg gctggtttat tgctgataaa   3420
tctggagccg gtgagcgtgg gtctcgcggt atcattgcag cactggggcc agatggtaag   3480
ccctcccgta tcgtagttat ctacacgacg gggagtcagg caactatgga tgaacgaaat   3540
agacagatcg ctgagatagg tgcctcactg attaagcatt ggtaactgtc agaccaagtt   3600
tactcatata ctttagat tgatttaaaa cttcattttt aatttaaaag gatctaggtg     3660
aagatccttt ttgataatct catgaccaaa atcccttaac gtgagttttc gttccactga   3720
gcgtcagacc ccgtagaaaa gatcaaagga tcttcttgag atcctttttt tctgcgcgta   3780
atctgctgct tgcaaacaaa aaaaccaccg ctaccagcgg tggtttgttt gccggatcaa   3840
gagctaccaa ctctttttcc gaaggtaact ggcttcagca gagcgcagat accaaatact   3900
gtccttctag tgtagccgta gttaggccac cacttcaaga actctgtagc accgcctaca   3960
tacctcgctc tgctaatcct gttaccagtg gctgctgcca gtggcgataa gtcgtgtctt   4020
accgggttgg actcaagacg atagttaccg gataaggcgc agcggtcggg ctgaacgggg   4080
ggttcgtgca cacagcccag cttggagcga acgacctaca ccgaactgag atacctacag   4140
cgtgagctat gagaaagcgc cacgcttccc gaagggagaa aggcggacag gtatccggta   4200
agcggcaggg tcggaacagg agagcgcacg aggagcttc caggggaaa cgcctggtat    4260
ctttatagtc ctgtcgggtt tcgccacctc tgacttgagc gtcgattttt gtgatgctcg   4320
tcagggggc ggagcctatg gaaaaacgcc agcaacgcgg cctttttacg gttcctggcc    4380
ttttgctggc cttttgctca catgttcttt cctgcgttat cccctgattc tgtggataac   4440
cgtattaccg cctttgagtg agctgatacc gctcgccgca gccgaacgac cgagcgcagc   4500
gagtcagtga gcgaggaagc ggaagagcgc ccaatacgca aaccgcctct ccccgcgcgt   4560
tggccgattc attaatgcag cagctgcgcg ctcgctcgct cactgaggcc gcccgggcaa   4620
agcccggggc tcgggcgacc tttggtcgcc cggcctcagt gagcgagcga gcgcgcagag   4680
agggagtggc caactccatc actaggggtt ccttgtagtt aatgattaac ccgccatgct   4740
acttatctac gtagccatgc tctaggacat tgattattga ctagttgagt tccgcgttac   4800
ataacttacg gtaaatggcc cgcctggctg accgcccaac gacccccgcc cattgacgtc   4860
aataatgacg tatgttccca tagtaacgcc aatagggact ttccattgac gtcaatgggt   4920
ggagtattta cggtaaactg cccacttggc agtacatcaa gtgtatcata tgccaagtac   4980
gccccctatt gacgtcaatg acggtaaatg gcccgcctgg cattatgccc agtacatgac   5040
cttatgggac tttcctactt ggcagtacat ctacgtatta gtcatcgcta ttaccatggt   5100
cgaggtgagc cccacgttct gcttcactct ccccatctcc cccccctccc cacccccaat   5160
tttgtattta ttttatttt aattatttg tgcagcgatg ggggcggggg ggggggggg     5220
cgcgcgccag gcggggcggg gcggggcgag ggcggggcg gggcgaggcg gagaggtgcg    5280
gcggcagcca atcagagcgg cgcgctccga aagtttcctt ttatggcgag gcggcggcgg   5340
cggcggccct ataaaaagcg aagcgcgcgg cgggcgggag tcgctgcgcg ctgccttcgc   5400
```

```
cccgtgcccc gctccgccgc cgcctcgcgc cgcccgcccc ggctctgact gaccgcgtta   5460
ctaaaacagg taagtccggc ctccgcgccg ggttttggcg cctcccgcgg gcgccccct    5520
cctcacggcg agcgctgcca cgtcagacga agggcgcagc gagcgtcctg atccttccgc   5580
ccggacgctc aggacagcgg cccgctgctc ataagactcg gccttagaac cccagtatca   5640
gcagaaggac attttaggac gggacttggg tgactctagg gcactggttt tctttccaga   5700
gagcggaaca ggcgaggaaa agtagtccct tctcggcgat tctgcggagg gatctccgtg   5760
gggcggtgaa cgccgatgat gcctctacta accatgttca tgttttcttt tttttttctac  5820
aggtcctggg tgacgaacag ggtaccgcca ccatggcgac gggttcaaga acttccctac   5880
ttcttgcatt tggcctgctt tgtttgccgt ggttacagga gggctcggca atggtgctgg   5940
cggcgccgct gctgctgggc tttctgctgc tggcgctgga actgcgcccg cgcggcgaag   6000
cggcggaagg cccggcggcg gcggcggcgg cggcggcggc ggcggcggcg gcgggcgtgg   6060
gcggcgaacg cagcagccgc ccggcgccga gcgtggcgcc ggaaccggat ggctgccgg    6120
tgtgcgtgtg gcgccagcat agccgcgaac tgcgcctgga aagcattaaa agccagattc   6180
tgagcaaact gcgcctgaaa gaagcgccga acattagccg cgaagtggtg aaacagctgc   6240
tgccgaaagc gccgccgctg cagcagattc tggatctgca tgattttcag ggcgatgcgc   6300
tgcagccgga agattttctg gaagaagatg aatatcatgc gaccaccgaa accgtgatta   6360
gcatggcgca ggaaaccgat ccggcggtgc agaccgatgg cagcccgctg tgctgccatt   6420
ttcattttag cccgaaagtg atgtttacca aagtgctgaa agcgcagctg tgggtgtatc   6480
tgcgcccggt gccgcgcccg gcgaccgtgt atctgcagat tctgcgcctg aaaccgctga   6540
ccggcgaagg caccgcgggc ggcggcggcg gcggccgccg ccatattcgc attcgcagcc   6600
tgaaaattga actgcatagc cgcagcggcc attggcagag cattgatttt aaacaggtgc   6660
tgcatagctg gtttcgccag ccgcagagca actggggcat tgaaattaac gcgtttgatc   6720
cgagcggcac cgatctggcg gtgaccagcc tgggcccggg cgcggaaggc ctgcatccgt   6780
ttatggaact gcgcgtgctg gaaaacacca aacgcagccg ccgcaacctg ggcctggatt   6840
gcgatgaaca tagcagcgaa agccgctgct gccgctatcc gctgaccgtg gattttgaag   6900
cgtttggctg ggattggatt attgcgccga aacgctataa agcgaactat tgcagcggcc   6960
agtgcgaata tatgtttatg cagaaatatc cgcatacca  tctggtgcag caggcgaacc   7020
cgcgcggcag cgcgggcccg tgctgcaccc cgaccaaaat gagcccgatt aacatgctgt   7080
attttaacga taaacagcag attatttatg gcaaaattcc gggcatggtg gtggatcgct   7140
gcggctgcag ctctagagat                                               7160
```

COMPOSITION FOR REGULATING PRODUCTION OF PROTEINS

This application contains a Sequence Listing electronically submitted via Patent Center to the United States Patent and Trademark Office as an XML Document file entitled "A8149868US-SequenceListing2.xml" created on 2024 Dec. 17 and having a size of 17,735 bytes. The information contained in the Sequence Listing is incorporated by reference herein.

TECHNICAL FIELD

The present disclosure generally relates to compositions for regulating the production of proteins. In particular, the present disclosure relates to compositions for regulating gene expression and, consequently, the production of proteins that act as cell growth and differentiation factors.

BACKGROUND

Aging can result in decreased levels of cell growth and differentiation factors.

This can result in reduced tissue repair after tissue injury.

As such, it may be desirable to establish therapies, treatments and/or interventions that may induce cell growth and differentiation factors to be endogenously produced in a subject.

SUMMARY

Some embodiments of the present disclosure relate to one or more compositions that upregulate the production of one or more sequences of messenger ribonucleic acid (mRNA). The sequences of mRNA may encode for the translation of a target biomolecule, thereby causing an increase in the bioavailability of the target biomolecule within a subject that is administered the one or more compositions. In some embodiments of the present disclosure, the target biomolecule is a protein such as bone morphogenetic protein 11 (BMP11).

In some embodiments of the present disclosure the compositions comprise a plasmid of deoxyribonucleic acid (DNA) that includes one or more insert sequences of nucleic acids that encode for the production of mRNA and a backbone sequence of nucleic acids that facilitates the introduction of the one or more insert sequences into one or more of a subject's cells where it is thereby expressed and/or replicated. Expression of the one or more insert sequences by one or more cells of the subject results in an increased production of the mRNA and, consequently, increased translation of the target biomolecule by one or more of the subject's cells.

Some embodiments of the present disclosure relate to a recombinant plasmid (RP). In some embodiments of the present disclosure, the RP comprises a nucleotide sequence of SEQ ID NO. 1 and SEQ ID NO. 2. The RP comprises a nucleotide sequence encoding for one or more nucleotide sequences encoding for an mRNA sequence that encodes for the protein BMP11.

Some embodiments of the present disclosure relate to a method of making a composition/target cell complex. The method comprises a step of administering an RP comprising SEQ ID NO. 1 and SEQ ID NO. 2 to a target cell for forming the composition/target cell complex, wherein the composition/target cell complex causes the target cell to increase the production of one or more sequences of mRNA that consequently increases the production of a target biomolecule.

Embodiments of the present disclosure relate to at least one approach for inducing the endogenous production of one or more sequences of mRNA that encodes for a target biomolecule, for example BMP11. A first approach utilizes gene vectors containing nucleotide sequences for increasing the endogenous production of one or more sequences of mRNA, which are complete or partial sequences of BMP11 and/or combinations thereof, which can be administered to a subject to increase the subject's production of one or more sequences of the mRNA.

DETAILED DESCRIPTION

Unless defined otherwise, all technical and scientific terms used therein have the meanings that would be commonly understood by one of skill in the art in the context of the present disclosure. Although any methods and materials similar or equivalent to those described therein can also be used in the practice or testing of the present disclosure, the preferred compositions, methods and materials are now described. All publications mentioned therein are incorporated therein by reference to disclose and describe the methods and/or materials in connection with which the publications are cited.

As used therein, the singular forms "a", "an", and "the" include plural references unless the context clearly dictates otherwise. For example, reference to "a composition" includes one or more compositions and reference to "a subject" or "the subject" includes one or more subjects.

As used therein, the terms "about" or "approximately" refer to within about 25%, preferably within about 20%, preferably within about 15%, preferably within about 10%, preferably within about 5% of a given value or range. It is understood that such a variation is always included in any given value provided therein, whether or not it is specifically referred to.

As used therein, the term "ameliorate" refers to improve and/or to make better and/or to make more satisfactory.

As used therein, the term "cell" refers to a single cell as well as a plurality of cells or a population of the same cell type or different cell types. Administering a composition to a cell includes in vivo, in vitro and ex vivo administrations and/or combinations thereof.

As used therein, the term "complex" refers to an association, either direct or indirect, between one or more particles of a composition and one or more target cells. This association results in a change in the metabolism of the target cell. As used therein, the phrase "change in metabolism" refers to an increase or a decrease in the one or more target cells' production of one or more proteins, and/or any post-translational modifications of one or more proteins.

As used therein, the term "composition" refers to a substance that, when administered to a subject, causes one or more chemical reactions and/or one or more physical reactions and/or one or more physiological reactions and/or one or more immunological reactions in the subject. In some embodiments of the present disclosure, the composition is a plasmid vector.

As used therein, the term "endogenous" refers to the production and/or modification of a molecule that originates within a subject.

As used therein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also used therein to refer to the functionality of a regulatory molecule, unless the context reasonably indicates otherwise.

As used therein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue, and/or biological fluids.

As used therein, the term "target biomolecule" refers to a protein molecule that is found within a subject.

As used therein, the term "target cell" refers to one or more cells and/or cell types that are affected, either directly or indirectly, by a biomolecule.

As used therein, the term "therapeutically effective amount" refers to the amount of the composition used that is of sufficient quantity to ameliorate, treat and/or inhibit one or more of a disease, disorder or a symptom thereof. The "therapeutically effective amount" will vary depending on the composition used, the route of administration of the composition and the severity of the disease, disorder or symptom thereof. The subject's age, weight and genetic make-up may also influence the amount of the composition that will be a therapeutically effective amount.

As used therein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used therein, the terms "unit dosage form" and "unit dose" refer to a physically discrete unit that is suitable as a unitary dose for patients. Each unit contains a predetermined quantity of the composition and optionally, one or more suitable pharmaceutically acceptable carriers, one or more excipients, one or more additional active ingredients, or combinations thereof. The amount of composition within each unit is a therapeutically effective amount.

Where a range of values is provided therein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, a composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered without a carrier, by a viral vector, by a protein coat, or by a lipid vesicle. In some embodiments of the present disclosure, the vector is an adeno-associated virus (AAV) vector.

In some embodiments of the present disclosure, the insert comprises one or more nucleotide sequences that encode for the production of at least one sequence of mRNA that increases the production of target biomolecules, such as a protein.

In some embodiments of the present disclosure, the target biomolecule is BMP11.

Some embodiments of the present disclosure relate to a composition that can be administered to a subject with a condition that results, directly or indirectly, from the dysregulated production of a biomolecule. When a therapeutically effective amount of the composition is administered to the subject, the production and/or functionality of one or more of the subject's biomolecules may change as a result.

In some embodiments of the present disclosure, the production and/or functionality of one or more of the subject's intermediary molecules may change in response to the subject receiving a therapeutic amount of the composition, thereby changing production of one or more DNA sequences, one or more RNA sequences, and/or one or more proteins that regulate the levels and/or functionality of the one or more intermediary molecules. The one or more intermediary molecules may regulate the subject's levels and/or functionality of the one or more biomolecules.

In some embodiments of the present disclosure, administering a therapeutic amount of the composition to a subject upregulates the production, functionality or both of one or more sequences of mRNA that each encode for one or more biomolecules.

In some embodiments of the present disclosure, the composition is an RP that may be used for gene therapy. The gene therapy is useful for increasing the subject's endogenous production of one or more sequences of mRNA that encode for a target biomolecule. For example, the RP can contain one or more nucleotide sequences that cause increased production of one or more nucleotide sequences that cause an increased production of one or more mRNA sequences that encode for one biomolecule, such as BMP11.

In some embodiments of the present disclosure, the delivery vehicle of the RP used for gene therapy may be a vector that comprises a virus that can be enveloped, or not (unenveloped), replication effective or not (replication ineffective), or combinations thereof. In some embodiments of the present disclosure, the vector is a virus that is not enveloped and not replication effective. In some embodiments of the present disclosure, the vector is a virus of the Parvoviridae family. In some embodiments of the present disclosure, the vector is a virus of the genus Dependoparvovirus. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

In some embodiments of the present disclosure, the delivery vehicle of the RP used for gene therapy may be a protein coat.

In some embodiments of the present disclosure, the delivery vehicle of the RP used for gene therapy may be a lipid vesicle.

The embodiments of the present disclosure also relate to administering a therapeutically effective amount of the composition. In some embodiments of the present disclosure, the therapeutically effective amount of the composition that is administered to a patient is between about 10 and about $1\times10^{16}$ TCID$_{50}$/kg (50% tissue culture infective dose per kilogram of the patient's body mass). In some embodiments of the present disclosure, the therapeutically effective amount of the composition that is administered to the patient is about $1\times10^{13}$ TCID$_{50}$/kg. In some embodiments of the present disclosure, the therapeutically effective amount of the composition that is administered to a patient is measured in TPC/kg (total particle count of the composition per kilogram of the patient's body mass). In some embodiments of the present disclosure, the therapeutically effective amount of the composition is between about 10 and about $1\times10^{16}$ TCP/kg.

Some embodiments of the present disclosure relate to an adeno-associated virus (AAV) genome consisting of an RP that, when operable inside a target cell, will cause the target cell to produce an mRNA sequence that upregulates the production of a biomolecule, with an example being BMP11. The RP is comprised of AAV2 inverted terminal repeats (ITRs), a composite CASI promoter, and a human growth hormone (HGH) signal peptide followed by a mRNA expression cassette encoding for BMP11, followed by a Woodchuck Hepatitis Virus post-transcriptional regulatory element (WPRE) and a Simian virus 40 (SV40) polyadenylation (polyA) signal.

```
SEQ ID NO. 1 (backbone sequence No. 1):
5'

AATCAACCTCTGGATTACAAAATTTGTGAAAGATTGACTGGTATTCTTAACTATGTT

GCTCCTTTTACGCTATGTGGATACGCTGCTTTAATGCCTTTGTATCATGCTATTGCTT

CCCGTATGGCTTTCATTTTCTCCTCCTTGTATAAATCCTGGTTGCTGTCTCTTTATGAG

GAGTTGTGGCCCGTTGTCAGGCAACGTGGCGTGGTGTGCACTGTGTTTGCTGACGCA

ACCCCCACTGGTTGGGGCATTGCCACCACCTGTCAGCTCCTTTCCGGGACTTTCGCTT

TCCCCCTCCCTATTGCCACGGCGGAACTCATCGCCGCCTGCCTTGCCCGCTGCTGGA

CAGGGGCTCGGCTGTTGGGCACTGACAATTCCGTGGTGTTGTCGGGGAAATCATCGT

CCTTTCCTTGGCTGCTCGCCTGTGTTGCCACCTGGATTCTGCGCGGGACGTCCTTCTG

CTACGTCCCTTCGGCCCTCAATCCAGCGGACCTTCCTTCCCGCGGCCTGCTGCCGGCT

CTGCGGCCTCTTCCGCGTCTTCGCCTTCGCCCTCAGACGAGTCGGATCTCCCTTTGGG

CCGCCTCCCCGCCTAAGCTTATCGATACCGTCGAGATCTAACTTGTTTATTGCAGCTT

ATAATGGTTACAAATAAAGCAATAGCATCACAAATTTCACAAATAAAGCATTTTTTT

CACTGCATTCTAGTTGTGGTTTGTCCAAACTCATCAATGTATCTTATCATGTCTGGAT

CTCGACCTCGACTAGAGCATGGCTACGTAGATAAGTAGCATGGCGGGTTAATCATTA

ACTACAAGGAACCCCTAGTGATGGAGTTGGCCACTCCCTCTCTGCGCGCTCGCTCGC

TCACTGAGGCCGGGCGACCAAAGGTCGCCCGACGCCCGGGCTTTGCCCGGGCGGCC

TCAGTGAGCGAGCGAGCGCGCCAGCTGGCGTAATAGCGAAGAGGCCCGCACCGATC

GCCCTTCCCAACAGTTGCGCAGCCTGAATGGCGAATGGAATTCCAGACGATTGAGC

GTCAAAATGTAGGTATTTCCATGAGCGTTTTTCCTGTTGCAATGGCTGGCGGTAATA

TTGTTCTGGATATTACCAGCAAGGCCGATAGTTTGAGTTCTTCTACTCAGGCAAGTG

ATGTTATTACTAATCAAAGAAGTATTGCGACAACGGTTAATTTGCGTGATGGACAGA

CTCTTTTACTCGGTGGCCTCACTGATTATAAAAACACTTCTCAGGATTCTGGCGTACC

GTTCCTGTCTAAAATCCCTTTAATCGGCCTCCTGTTTAGCTCCCGCTCTGATTCTAAC

GAGGAAAGCACGTTATACGTGCTCGTCAAAGCAACCATAGTACGCGCCCTGTAGCG

GCGCATTAAGCGCGGCGGGTGTGGTGGTTACGCGCAGCGTGACCGCTACACTTGCC

AGCGCCCTAGCGCCCGCTCCTTTCGCTTTCTTCCCTTCCTTTCTCGCCACGTTCGCCG

GCTTTCCCCGTCAAGCTCTAAATCGGGGGCTCCCTTTAGGGTTCCGATTTAGTGCTTT

ACGGCACCTCGACCCCAAAAAACTTGATTAGGGTGATGGTTCACGTAGTGGGCCATC

GCCCTGATAGACGGTTTTTCGCCCTTTGACGTTGGAGTCCACGTTCTTTAATAGTGGA
```

-continued

```
CTCTTGTTCCAAACTGGAACAACACTCAACCCTATCTCGGTCTATTCTTTTGATTTAT

AAGGGATTTTGCCGATTTCGGCCTATTGGTTAAAAAATGAGCTGATTTAACAAAAAT

TTAACGCGAATTTTAACAAAATATTAACGTTTACAATTTAAATATTTGCTTATACAAT

CTTCCTGTTTTTGGGGCTTTTCTGATTATCAACCGGGGTACATATGATTGACATGCTA

GTTTTACGATTACCGTTCATCGATTCTCTTGTTTGCTCCAGACTCTCAGGCAATGACC

TGATAGCCTTTGTAGAGACCTCTCAAAAATAGCTACCCTCTCCGGCATGAATTTATC

AGCTAGAACGGTTGAATATCATATTGATGGTGATTTGACTGTCTCCGGCCTTTCTCAC

CCGTTTGAATCTTTACCTACACATTACTCAGGCATTGCATTTAAAATATATGAGGGTT

CTAAAAATTTTTATCCTTGCGTTGAAATAAAGGCTTCTCCCGCAAAAGTATTACAGG

GTCATAATGTTTTGGTACAACCGATTTAGCTTTATGCTCTGAGGCTTTATTGCTTAA

TTTTGCTAATTCTTTGCCTTGCCTGTATGATTTATTGGATGTTGGAATTCCTGATGCG

GTATTTTCTCCTTACGCATCTGTGCGGTATTTCACACCGCATATGGTGCACTCTCAGT

ACAATCTGCTCTGATGCCGCATAGTTAAGCCAGCCCCGACACCCGCCAACACCCGCT

GACGCGCCCTGACGGGCTTGTCTGCTCCCGGCATCCGCTTACAGACAAGCTGTGACC

GTCTCCGGGAGCTGCATGTGTCAGAGGTTTTCACCGTCATCACCGAAACGCGCGAGA

CGAAAGGGCCTCGTGATACGCCTATTTTTATAGGTTAATGTCATGATAATAATGGTT

TCTTAGACGTCAGGTGGCACTTTTCGGGGAAATGTGCGCGGAACCCCTATTTGTTTA

TTTTTCTAAATACATTCAAATATGTATCCGCTCATGAGACAATAACCCTGATAAATG

CTTCAATAATATTGAAAAAGGAAGAGTATGAGTATTCAACATTTCCGTGTCGCCCTT

ATTCCCTTTTTTGCGGCATTTTGCCTTCCTGTTTTTGCTCACCCAGAAACGCTGGTGA

AAGTAAAAGATGCTGAAGATCAGTTGGGTGCACGAGTGGGTTACATCGAACTGGAT

CTCAACAGCGGTAAGATCCTTGAGAGTTTTCGCCCCGAAGAACGTTTTCCAATGATG

AGCACTTTTAAAGTTCTGCTATGTGGCGCGGTATTATCCCGTATTGACGCCGGGCAA

GAGCAACTCGGTCGCCGCATACACTATTCTCAGAATGACTTGGTTGAGTACTCACCA

GTCACAGAAAAGCATCTTACGGATGGCATGACAGTAAGAGAATTATGCAGTGCTGC

CATAACCATGAGTGATAACACTGCGGCCAACTTACTTCTGACAACGATCGGAGGAC

CGAAGGAGCTAACCGCTTTTTTGCACAACATGGGGGATCATGTAACTCGCCTTGATC

GTTGGGAACCGGAGCTGAATGAAGCCATACCAAACGACGAGCGTGACACCACGATG

CCTGTAGCAATGGCAACAACGTTGCGCAAACTATTAACTGGCGAACTACTTACTCTA

GCTTCCCGGCAACAATTAATAGACTGGATGGAGGCGGATAAAGTTGCAGGACCACT

TCTGCGCTCGGCCCTTCCGGCTGGCTGGTTTATTGCTGATAAATCTGGAGCCGGTGA

GCGTGGGTCTCGCGGTATCATTGCAGCACTGGGGCCAGATGGTAAGCCCTCCCGTAT

CGTAGTTATCTACACGACGGGGAGTCAGGCAACTATGGATGAACGAAATAGACAGA

TCGCTGAGATAGGTGCCTCACTGATTAAGCATTGGTAACTGTCAGACCAAGTTTACT

CATATATACTTTAGATTGATTTAAAACTTCATTTTTAATTTAAAAGGATCTAGGTGAA

GATCCTTTTTGATAATCTCATGACCAAAATCCCTTAACGTGAGTTTTCGTTCCACTGA

GCGTCAGACCCCGTAGAAAAGATCAAAGGATCTTCTTGAGATCCTTTTTTTCTGCGC

GTAATCTGCTGCTTGCAAACAAAAAAACCACCGCTACCAGCGGTGGTTTGTTTGCCG

GATCAAGAGCTACCAACTCTTTTTCCGAAGGTAACTGGCTTCAGCAGAGCGCAGATA

CCAAATACTGTCCTTCTAGTGTAGCCGTAGTTAGGCCACCACTTCAAGAACTCTGTA
```

-continued

```
GCACCGCCTACATACCTCGCTCTGCTAATCCTGTTACCAGTGGCTGCTGCCAGTGGC
GATAAGTCGTGTCTTACCGGGTTGGACTCAAGACGATAGTTACCGGATAAGGCGCA
GCGGTCGGGCTGAACGGGGGGTTCGTGCACACAGCCCAGCTTGGAGCGAACGACCT
ACACCGAACTGAGATACCTACAGCGTGAGCTATGAGAAAGCGCCACGCTTCCCGAA
GGGAGAAAGGCGGACAGGTATCCGGTAAGCGGCAGGGTCGGAACAGGAGAGCGCA
CGAGGGAGCTTCCAGGGGGAAACGCCTGGTATCTTTATAGTCCTGTCGGGTTTCGCC
ACCTCTGACTTGAGCGTCGATTTTTGTGATGCTCGTCAGGGGGCGGAGCCTATGGA
AAAACGCCAGCAACGCGGCCTTTTTACGGTTCCTGGCCTTTTGCTGGCCTTTTGCTCA
CATGTTCTTTCCTGCGTTATCCCCTGATTCTGTGGATAACCGTATTACCGCCTTTGAG
TGAGCTGATACCGCTCGCCGCAGCCGAACGACCGAGCGCAGCGAGTCAGTGAGCGA
GGAAGCGGAAGAGCGCCCAATACGCAAACCGCCTCTCCCCGCGCGTTGGCCGATTC
ATTAATGCAGCAGCTGCGCGCTCGCTCGCTCACTGAGGCCGCCCGGGCAAAGCCCG
GGCGTCGGGCGACCTTTGGTCGCCCGGCCTCAGTGAGCGAGCGAGCGCGCAGAGAG
GGAGTGGCCAACTCCATCACTAGGGGTTCCTTGTAGTTAATGATTAACCCGCCATGC
TACTTATCTACGTAGCCATGCTCTAGGACATTGATTATTGACTAGTGGAGTTCCGCGT
TACATAACTTACGGTAAATGGCCCGCCTGGCTGACCGCCCAACGACCCCCGCCCATT
GACGTCAATAATGACGTATGTTCCCATAGTAACGCCAATAGGGACTTTCCATTGACG
TCAATGGGTGGAGTATTTACGGTAAACTGCCCACTTGGCAGTACATCAAGTGTATCA
TATGCCAAGTACGCCCCCTATTGACGTCAATGACGGTAAATGGCCCGCCTGGCATTA
TGCCCAGTACATGACCTTATGGGACTTTCCTACTTGGCAGTACATCTACGTATTAGTC
ATCGCTATTACCATGGTCGAGGTGAGCCCCACGTTCTGCTTCACTCTCCCCATCTCCC
CCCCCTCCCCACCCCCAATTTTGTATTTATTTATTTTTTAATTATTTTGTGCAGCGATG
GGGGCGGGGGGGGGGGGGCGCGCGCCAGGCGGGGGGGGCGGGGCGAGGGGC
GGGGCGGGGCGAGGCGGAGAGGTGCGGCGGCAGCCAATCAGAGCGGCGCGCTCCG
AAAGTTTCCTTTTATGGCGAGGCGGCGGCGGCGGCGGCCCTATAAAAAGCGAAGCG
CGCGGCGGGCGGGAGTCGCTGCGCGCTGCCTTCGCCCCGTGCCCCGCTCCGCCGCCG
CCTCGCGCCGCCCGCCCCGGCTCTGACTGACCGCGTTACTAAAACAGGTAAGTCCGG
CCTCCGCGCCGGGTTTTGGCGCCTCCCGCGGGCGCCCCCCTCCTCACGGCGAGCGCT
GCCACGTCAGACGAAGGGCGCAGCGAGCGTCCTGATCCTTCCGCCCGGACGCTCAG
GACAGCGGCCCGCTGCTCATAAGACTCGGCCTTAGAACCCCAGTATCAGCAGAAGG
ACATTTTAGGACGGGACTTGGGTGACTCTAGGGCACTGGTTTTCTTTCCAGAGAGCG
GAACAGGCGAGGAAAAGTAGTCCCTTCTCGGCGATTCTGCGGAGGGATCTCCGTGG
GGCGGTGAACGCCGATGATGCCTCTACTAACCATGTTCATGTTTTCTTTTTTTTCTA
CAGGTCCTGGGTGACGAACAGGGTACCGCCACCATGGCGACGGGTTCAAGAACTTC
CCTACTTCTTGCATTTGGCCTGCTTTGTTTGCCGTGGTTACAGGAGGGCTCGGCA
3'

SEQ ID NO. 2 (mRNA expression cassette No. 2 - BMP11):
5'
ATGGTGCTGGCGGCGCCGCTGCTGCTGGGCTTTCTGCTGCTGGCGCTGGAACTGCGC
CCGCGCGGCGAAGCGGCGGAAGGCCCGGCGGCGGCGGCGGCGGCGGCGGCGGCGG
CGGCGGCGGCGGGCGTGGGCGGCGAACGCAGCAGCCGCCCGGCGCCGAGCGTGGC
```

-continued

GCCGGAACCGGATGGCTGCCCGGTGTGCGTGTGGCGCCAGCATAGCCGCGAACTGC

GCCTGGAAAGCATTAAAAGCCAGATTCTGAGCAAACTGCGCCTGAAAGAAGCGCCG

AACATTAGCCGCGAAGTGGTGAAACAGCTGCTGCCGAAAGCGCCGCCGCTGCAGCA

GATTCTGGATCTGCATGATTTTCAGGGCGATGCGCTGCAGCCGGAAGATTTTCTGGA

AGAAGATGAATATCATGCGACCACCGAAACCGTGATTAGCATGGCGCAGGAAACCG

ATCCGGCGGTGCAGACCGATGGCAGCCCGCTGTGCTGCCATTTTCATTTTAGCCCGA

AAGTGATGTTTACCAAAGTGCTGAAAGCGCAGCTGTGGGTGTATCTGCGCCCGGTGC

CGCGCCCGGCGACCGTGTATCTGCAGATTCTGCGCCTGAAACCGCTGACCGGCGAA

GGCACCGCGGGCGGCGGCGGCGGCGGCCGCCGCCATATTCGCATTCGCAGCCTGAA

AATTGAACTGCATAGCCGCAGCGGCCATTGGCAGAGCATTGATTTTAAACAGGTGCT

GCATAGCTGGTTTCGCCAGCCGCAGAGCAACTGGGGCATTGAAATTAACGCGTTTGA

TCCGAGCGGCACCGATCTGGCGGTGACCAGCCTGGGCCCGGGCGCGGAAGGCCTGC

ATCCGTTTATGGAACTGCGCGTGCTGGAAAACACCAAACGCAGCCGCCGCAACCTG

GGCCTGGATTGCGATGAACATAGCAGCGAAAGCCGCTGCTGCCGCTATCCGCTGAC

CGTGGATTTTGAAGCGTTTGGCTGGGATTGGATTATTGCGCCGAAACGCTATAAAGC

GAACTATTGCAGCGGCCAGTGCGAATATATGTTTATGCAGAAATATCCGCATACCCA

TCTGGTGCAGCAGGCGAACCCGCGCGGCAGCGCGGGCCCGTGCTGCACCCCGACCA

AAATGAGCCCGATTAACATGCTGTATTTTAACGATAAACAGCAGATTATTTATGGCA

AAATTCCGGGCATGGTGGTGGATCGCTGCGGCTGCAGCTCTAGAGAT

3'

SEQ ID NO. 3 = SEQ ID NO. 1 + SEQ ID NO. 2
5'

AATCAACCTCTGGATTACAAAATTTGTGAAAGATTGACTGGTATTCTTAACTATGTT

GCTCCTTTTACGCTATGTGGATACGCTGCTTTAATGCCTTTGTATCATGCTATTGCTT

CCCGTATGGCTTTCATTTTCTCCTCCTTGTATAAATCCTGGTTGCTGTCTCTTTATGAG

GAGTTGTGGCCCGTTGTCAGGCAACGTGGCGTGGTGTGCACTGTGTTTGCTGACGCA

ACCCCCACTGGTTGGGGCATTGCCACCACCTGTCAGCTCCTTTCCGGGACTTTCGCTT

TCCCCCTCCCTATTGCCACGGCGGAACTCATCGCCGCCTGCCTTGCCCGCTGCTGGA

CAGGGGCTCGGCTGTTGGGCACTGACAATTCCGTGGTGTTGTCGGGGAAATCATCGT

CCTTTCCTTGGCTGCTCGCCTGTGTTGCCACCTGGATTCTGCGCGGGACGTCCTTCTG

CTACGTCCCTTCGGCCCTCAATCCAGCGGACCTTCCTTCCCGCGGCCTGCTGCCGGCT

CTGCGGCCTCTTCCGCGTCTTCGCCTTCGCCCTCAGACGAGTCGGATCTCCCTTTGGG

CCGCCTCCCCGCCTAAGCTTATCGATACCGTCGAGATCTAACTTGTTTATTGCAGCTT

ATAATGGTTACAAATAAAGCAATAGCATCACAAATTTCACAAATAAAGCATTTTTTT

CACTGCATTCTAGTTGTGGTTTGTCCAAACTCATCAATGTATCTTATCATGTCTGGAT

CTCGACCTCGACTAGAGCATGGCTACGTAGATAAGTAGCATGGCGGGTTAATCATTA

ACTACAAGGAACCCCTAGTGATGGAGTTGGCCACTCCCTCTCTGCGCGCTCGCTCGC

TCACTGAGGCCGGGCGACCAAAGGTCGCCCGACGCCCGGGCTTTGCCCGGGCGGCC

TCAGTGAGCGAGCGAGCGCGCCAGCTGGCGTAATAGCGAAGAGGCCCGCACCGATC

GCCCTTCCCAACAGTTGCGCAGCCTGAATGGCGAATGGAATTCCAGACGATTGAGC

GTCAAAATGTAGGTATTTCCATGAGCGTTTTTCCTGTTGCAATGGCTGGCGGTAATA

```
TTGTTCTGGATATTACCAGCAAGGCCGATAGTTTGAGTTCTTCTACTCAGGCAAGTG
ATGTTATTACTAATCAAAGAAGTATTGCGACAACGGTTAATTTGCGTGATGGACAGA
CTCTTTTACTCGGTGGCCTCACTGATTATAAAAACACTTCTCAGGATTCTGGCGTACC
GTTCCTGTCTAAAATCCCTTTAATCGGCCTCCTGTTTAGCTCCCGCTCTGATTCTAAC
GAGGAAAGCACGTTATACGTGCTCGTCAAAGCAACCATAGTACGCGCCCTGTAGCG
GCGCATTAAGCGCGGCGGGTGTGGTGGTTACGCGCAGCGTGACCGCTACACTTGCC
AGCGCCCTAGCGCCCGCTCCTTTCGCTTTCTTCCCTTCCTTTCTCGCCACGTTCGCCG
GCTTTCCCCGTCAAGCTCTAAATCGGGGGCTCCCTTTAGGGTTCCGATTTAGTGCTTT
ACGGCACCTCGACCCCAAAAAACTTGATTAGGGTGATGGTTCACGTAGTGGGCCATC
GCCCTGATAGACGGTTTTTCGCCCTTTGACGTTGGAGTCCACGTTCTTTAATAGTGGA
CTCTTGTTCCAAACTGGAACAACACTCAACCCTATCTCGGTCTATTCTTTTGATTTAT
AAGGGATTTTGCCGATTTCGGCCTATTGGTTAAAAAATGAGCTGATTTAACAAAAAT
TTAACGCGAATTTTAACAAAATATTAACGTTTACAATTTAAATATTTGCTTATACAAT
CTTCCTGTTTTTGGGGCTTTTCTGATTATCAACCGGGGTACATATGATTGACATGCTA
GTTTTACGATTACCGTTCATCGATTCTCTTGTTTGCTCCAGACTCTCAGGCAATGACC
TGATAGCCTTTGTAGAGACCTCTCAAAAATAGCTACCCTCTCCGGCATGAATTTATC
AGCTAGAACGGTTGAATATCATATTGATGGTGATTTGACTGTCTCCGGCCTTTCTCAC
CCGTTTGAATCTTTACCTACACATTACTCAGGCATTGCATTTAAAATATATGAGGGTT
CTAAAAATTTTTATCCTTGCGTTGAAATAAAGGCTTCTCCCGCAAAAGTATTACAGG
GTCATAATGTTTTTGGTACAACCGATTTAGCTTTATGCTCTGAGGCTTTATTGCTTAA
TTTTGCTAATTCTTTGCCTTGCCTGTATGATTTATTGGATGTTGGAATTCCTGATGCG
GTATTTTCTCCTTACGCATCTGTGCGGTATTTCACACCGCATATGGTGCACTCTCAGT
ACAATCTGCTCTGATGCCGCATAGTTAAGCCAGCCCCGACACCCGCCAACACCCGCT
GACGCGCCCTGACGGGCTTGTCTGCTCCCGGCATCCGCTTACAGACAAGCTGTGACC
GTCTCCGGGAGCTGCATGTGTCAGAGGTTTTCACCGTCATCACCGAAACGCGCGAGA
CGAAAGGGCCTCGTGATACGCCTATTTTTATAGGTTAATGTCATGATAATAATGGTT
TCTTAGACGTCAGGTGGCACTTTTCGGGGAAATGTGCGCGGAACCCCTATTTGTTTA
TTTTTCTAAATACATTCAAATATGTATCCGCTCATGAGACAATAACCCTGATAAATG
CTTCAATAATATTGAAAAAGGAAGAGTATGAGTATTCAACATTTCCGTGTCGCCCTT
ATTCCCTTTTTTGCGGCATTTTGCCTTCCTGTTTTTGCTCACCCAGAAACGCTGGTGA
AAGTAAAAGATGCTGAAGATCAGTTGGGTGCACGAGTGGGTTACATCGAACTGGAT
CTCAACAGCGGTAAGATCCTTGAGAGTTTTCGCCCCGAAGAACGTTTTCCAATGATG
AGCACTTTTAAAGTTCTGCTATGTGGCGCGGTATTATCCCGTATTGACGCCGGGCAA
GAGCAACTCGGTCGCCGCATACACTATTCTCAGAATGACTTGGTTGAGTACTCACCA
GTCACAGAAAAGCATCTTACGGATGGCATGACAGTAAGAGAATTATGCAGTGCTGC
CATAACCATGAGTGATAACACTGCGGCCAACTTACTTCTGACAACGATCGGAGGAC
CGAAGGAGCTAACCGCTTTTTTGCACAACATGGGGGATCATGTAACTCGCCTTGATC
GTTGGGAACCGGAGCTGAATGAAGCCATACCAAACGACGAGCGTGACACCACGATG
CCTGTAGCAATGGCAACAACGTTGCGCAAACTATTAACTGGCGAACTACTTACTCTA
GCTTCCCGGCAACAATTAATAGACTGGATGGAGGCGGATAAAGTTGCAGGACCACT
TCTGCGCTCGGCCCTTCCGGCTGGCTGGTTTATTGCTGATAAATCTGGAGCCGGTGA
```

-continued

```
GCGTGGGTCTCGCGGTATCATTGCAGCACTGGGGCCAGATGGTAAGCCCTCCCGTAT
CGTAGTTATCTACACGACGGGGAGTCAGGCAACTATGGATGAACGAAATAGACAGA
TCGCTGAGATAGGTGCCTCACTGATTAAGCATTGGTAACTGTCAGACCAAGTTTACT
CATATATACTTTAGATTGATTTAAAACTTCATTTTTAATTTAAAAGGATCTAGGTGAA
GATCCTTTTTGATAATCTCATGACCAAAATCCCTTAACGTGAGTTTTCGTTCCACTGA
GCGTCAGACCCCGTAGAAAAGATCAAAGGATCTTCTTGAGATCCTTTTTTCTGCGC
GTAATCTGCTGCTTGCAAACAAAAAAACCACCGCTACCAGCGGTGGTTTGTTTGCCG
GATCAAGAGCTACCAACTCTTTTTCCGAAGGTAACTGGCTTCAGCAGAGCGCAGATA
CCAAATACTGTCCTTCTAGTGTAGCCGTAGTTAGGCCACCACTTCAAGAACTCTGTA
GCACCGCCTACATACCTCGCTCTGCTAATCCTGTTACCAGTGGCTGCTGCCAGTGGC
GATAAGTCGTGTCTTACCGGGTTGGACTCAAGACGATAGTTACCGGATAAGGCGCA
GCGGTCGGGCTGAACGGGGGGTTCGTGCACACAGCCCAGCTTGGAGCGAACGACCT
ACACCGAACTGAGATACCTACAGCGTGAGCTATGAGAAAGCGCCACGCTTCCCGAA
GGGAGAAAGGCGGACAGGTATCCGGTAAGCGGCAGGGTCGGAACAGGAGAGCGCA
CGAGGGAGCTTCCAGGGGGAAACGCCTGGTATCTTTATAGTCCTGTCGGGTTTCGCC
ACCTCTGACTTGAGCGTCGATTTTTGTGATGCTCGTCAGGGGGGCGGAGCCTATGGA
AAAACGCCAGCAACGCGGCCTTTTTACGGTTCCTGGCCTTTTGCTGGCCTTTTGCTCA
CATGTTCTTTCCTGCGTTATCCCCTGATTCTGTGGATAACCGTATTACCGCCTTTGAG
TGAGCTGATACCGCTCGCCGCAGCCGAACGACCGAGCGCAGCGAGTCAGTGAGCGA
GGAAGCGGAAGAGCGCCCAATACGCAAACCGCCTCTCCCCGCGCGTTGGCCGATTC
ATTAATGCAGCAGCTGCGCGCTCGCTCGCTCACTGAGGCCGCCCGGGCAAAGCCCG
GGCGTCGGGCGACCTTTGGTCGCCCGGCCTCAGTGAGCGAGCGAGCGCGCAGAGAG
GGAGTGGCCAACTCCATCACTAGGGGTTCCTTGTAGTTAATGATTAACCCGCCATGC
TACTTATCTACGTAGCCATGCTCTAGGACATTGATTATTGACTAGTGGAGTTCCGCGT
TACATAACTTACGGTAAATGGCCCGCCTGGCTGACCGCCCAACGACCCCCGCCCATT
GACGTCAATAATGACGTATGTTCCCATAGTAACGCCAATAGGGACTTTCCATTGACG
TCAATGGGTGGAGTATTTACGGTAAACTGCCCACTTGGCAGTACATCAAGTGTATCA
TATGCCAAGTACGCCCCCTATTGACGTCAATGACGGTAAATGGCCCGCCTGGCATTA
TGCCCAGTACATGACCTTATGGGACTTTCCTACTTGGCAGTACATCTACGTATTAGTC
ATCGCTATTACCATGGTCGAGGTGAGCCCCACGTTCTGCTTCACTCTCCCCATCTCCC
CCCCCTCCCCACCCCCAATTTTGTATTTATTTATTTTTTAATTATTTTGTGCAGCGATG
GGGGCGGGGGGGGGGGGCGCGCGCCAGGCGGGGCGGGGCGGGGCGAGGGGC
GGGGCGGGGCGAGGCGGAGAGGTGCGGCGGCAGCCAATCAGAGCGGCGCGCTCCG
AAAGTTTCCTTTTATGGCGAGGCGGCGGCGGCGGCGGCCCTATAAAAAGCGAAGCG
CGCGGCGGGCGGGAGTCGCTGCGCGCTGCCTTCGCCCCGTGCCCCGCTCCGCCGCCG
CCTCGCGCCGCCCGCCCCGGCTCTGACTGACCGCGTTACTAAAACAGGTAAGTCCGG
CCTCCGCGCCGGGTTTTGGCGCCTCCCGCGGGCGCCCCCCTCCTCACGGCGAGCGCT
GCCACGTCAGACGAAGGGCGCAGCGAGCGTCCTGATCCTTCCGCCCGGACGCTCAG
GACAGCGGCCCGCTGCTCATAAGACTCGGCCTTAGAACCCCAGTATCAGCAGAAGG
ACATTTTAGGACGGGACTTGGGTGACTCTAGGGCACTGGTTTTCTTTCCAGAGAGCG
```

-continued
```
GAACAGGCGAGGAAAAGTAGTCCCTTCTCGGCGATTCTGCGGAGGGATCTCCGTGG

GGCGGTGAACGCCGATGATGCCTCTACTAACCATGTTCATGTTTTCTTTTTTTTCTA

CAGGTCCTGGGTGACGAACAGGGTACCGCCACCATGGCGACGGGTTCAAGAACTTC

CCTACTTCTTGCATTTGGCCTGCTTTGTTTGCCGTGGTTACAGGAGGGCTCGGCAATG

GTGCTGGCGGCGCCGCTGCTGCTGGGCTTTCTGCTGCTGGCGCTGGAACTGCGCCCG

CGCGGCGAAGCGGCGGAAGGCCCGGCGGCGGCGGCGGCGGCGGCGGCGGCGGCGG

CGGCGGCGGGCGTGGGCGGCGAACGCAGCAGCCGCCCGGCGCCGAGCGTGGCGCC

GGAACCGGATGGCTGCCCGGTGTGCGTGTGGCGCCAGCATAGCCGCGAACTGCGCC

TGGAAAGCATTAAAAGCCAGATTCTGAGCAAACTGCGCCTGAAAGAAGCGCCGAAC

ATTAGCCGCGAAGTGGTGAAACAGCTGCTGCCGAAAGCGCCGCCGCTGCAGCAGAT

TCTGGATCTGCATGATTTTCAGGGCGATGCGCTGCAGCCGGAAGATTTTCTGGAAGA

AGATGAATATCATGCGACCACCGAAACCGTGATTAGCATGGCGCAGGAAACCGATC

CGGCGGTGCAGACCGATGGCAGCCCGCTGTGCTGCCATTTTCATTTTAGCCCGAAAG

TGATGTTTACCAAAGTGCTGAAAGCGCAGCTGTGGGTGTATCTGCGCCCGGTGCCGC

GCCCGGCGACCGTGTATCTGCAGATTCTGCGCCTGAAACCGCTGACCGGCGAAGGC

ACCGCGGGCGGCGCGGCGGCGGCCGCCGCCGCATATTCGCATTCGCAGCCTGAAAAT

TGAACTGCATAGCCGCAGCGGCCATTGGCAGAGCATTGATTTTAAACAGGTGCTGCA

TAGCTGGTTTCGCCAGCCGCAGAGCAACTGGGGCATTGAAATTAACGCGTTTGATCC

GAGCGGCACCGATCTGGCGGTGACCAGCCTGGGCCCGGGCGCGGAAGGCCTGCATC

CGTTTATGGAACTGCGCGTGCTGGAAAACACCAAACGCAGCCGCCGCAACCTGGGC

CTGGATTGCGATGAACATAGCAGCGAAAGCCGCTGCTGCCGCTATCCGCTGACCGT

GGATTTTGAAGCGTTTGGCTGGGATTGGATTATTGCGCCGAAACGCTATAAAGCGAA

CTATTGCAGCGGCCAGTGCGAATATATGTTTATGCAGAAATATCCGCATACCCATCT

GGTGCAGCAGGCGAACCCGCGCGGCAGCGCGGGCCCGTGCTGCACCCCGACCAAAA

TGAGCCCGATTAACATGCTGTATTTTAACGATAAACAGCAGATTATTTATGGCAAAA

TTCCGGGCATGGTGGTGGATCGCTGCGGCTGCAGCTCTAGAGAT

3'
```

As will be appreciated by those skilled in the art, because the recombinant plasmid is a circular vector, the one or more sequences of the mRNA expression cassettes may be connected at the 3' end of SEQ ID NO. 1, as shown in SEQ ID NO. 3 or at the 5' end of SEQ ID NO. 1.

As will be appreciated by those skilled in the art, a perfect match of nucleotides with each of the mRNA expression cassette sequences is not necessary in order to have the desired result of increased bioavailability of the target biomolecule as a result of the target cell producing the mRNA sequence that code for the expression of the target biomolecule. In some embodiments of the present disclosure, about 80% to about 100% nucleotide sequence matching with each of the mRNA expression cassettes causes the desired result. In some embodiments of the present disclosure, about 85% to about 100% nucleotide sequence matching with each of the mRNA expression cassettes causes the desired result. In some embodiments of the present disclosure, about 90% to about 100% nucleotide sequence matching with each of the mRNA expression cassettes causes the desired result. In some embodiments of the present disclosure, about 95% to about 100% nucleotide sequence matching with each of the mRNA expression cassettes causes the desired result.

Example 1—Expression Cassette

Expression cassettes for expressing mRNA were synthesized. The synthesized mRNA expression cassettes were cloned into the pAVA-00200 plasmid backbone containing the CASI promoter, multiple cloning site (MCS), Woodchuck Hepatitis Virus post-transcriptional regulatory element (WPRE), and Simian virus 40 (SV40) polyadenylation (polyA) sequence, all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each mRNA expression cassette was amplified by polymerase chain reaction (PCR) using Taq polymerase and the PCR products were gel purified and the bands on interest were also excised and purified using a gel extraction kit. These PCR products contained the mRNA expression cassettes in addition to 15 base pair 5' and 3' overhangs that aligned with the ends of the linearized pAVA-00200 backbone. Using in-fusion cloning, the amplified mRNA expression cassettes were integrated with the pAVA-00200 backbone via homologous recombination. The resulting RP contained the following: 5' ITR, CASI promoter, mRNA expression cassette, WPRE, SV40 polyA and ITR 3'.

The invention claimed is:

1. A composition that comprises a recombinant plasmid (RP) comprising a sequence of nucleotides with 95-100% identity to the nucleotide sequence of SEQ ID NO. 2, wherein the sequence of nucleotides encodes for a sequence of messenger ribonucleic acid (mRNA) that encodes for a bone morphogenetic protein 11 (BMP11).

2. The composition of claim 1, wherein the RP is encased in a protein coat, a lipid vesicle, or any combination thereof.

3. The composition of claim 1, wherein the RP is configured to be delivered to a target cell.

4. The composition of claim 1, wherein the RP is encased in a viral vector.

5. The composition of claim 4, wherein the viral vector is a double-stranded DNA virus, a single-stranded DNA virus, a single-stranded RNA virus, or a double-stranded RNA virus.

6. The composition of claim 4, wherein the viral vector is an adeno-associated virus.

7. A composition that comprises a RP comprising a sequence of nucleotides with 95-100% identity to the nucleotide sequence of SEQ ID NO. 3, wherein the sequence of nucleotides encodes for a sequence of mRNA that encodes for a BMP11.

* * * * *